(12) United States Patent
Du Tertre et al.

(10) Patent No.: US 8,979,360 B2
(45) Date of Patent: Mar. 17, 2015

(54) DEVICE EVALUATING THERMOMECHANICAL FATIGUE OF A MATERIAL

(75) Inventors: Alban Du Tertre, Vernon (FR); Alain Pyre, Saint Just (FR); Didier Guichard, Menilles (FR); Daniel Cornu, Mantes la Jolie (FR); Christophe Verdy, Evette-Salbert (FR); Christian Coddet, Giromagny (FR)

(73) Assignee: SNECMA, Paris (FR)

( * ) Notice: Subject to any disclaimer, the term of this patent is extended or adjusted under 35 U.S.C. 154(b) by 282 days.

(21) Appl. No.: 13/642,022

(22) PCT Filed: Apr. 20, 2011

(86) PCT No.: PCT/FR2011/050905
§ 371 (c)(1),
(2), (4) Date: Jan. 22, 2013

(87) PCT Pub. No.: WO2011/131906
PCT Pub. Date: Oct. 27, 2011

(65) Prior Publication Data
US 2013/0121368 A1    May 16, 2013

(30) Foreign Application Priority Data
Apr. 23, 2010   (FR) ..................................... 10 53118

(51) Int. Cl.
| G01N 25/00 | (2006.01) |
| G01N 25/72 | (2006.01) |
| F02K 9/96  | (2006.01) |
| G01N 3/60  | (2006.01) |

(52) U.S. Cl.
CPC   *G01N 25/72* (2013.01); *F02K 9/96* (2013.01); *G01N 3/60* (2013.01); *G01N 2203/0222* (2013.01); *G01N 2203/0226* (2013.01); *G01N 2203/0242* (2013.01)
USPC ................................ 374/5; 374/208; 374/141

(58) Field of Classification Search
USPC ...................................................... 374/5, 208
See application file for complete search history.

(56) References Cited

U.S. PATENT DOCUMENTS

| 3,029,635 A | 4/1962 | Fetz |
| 3,709,026 A | 1/1973 | Rhodes et al. |
| 7,645,070 B2 * | 1/2010 | Atwood et al. ............... 374/137 |
| 2004/0042527 A1 * | 3/2004 | Block et al. ..................... 374/29 |
| 2004/0069451 A1 * | 4/2004 | Meyer .......................... 165/80.2 |

(Continued)

FOREIGN PATENT DOCUMENTS

| DE | 10 2006 009 465 | 9/2007 |
| EP | 0 588 739 | 3/1994 |

(Continued)

OTHER PUBLICATIONS

International Search Report Issued on Aug. 24, 2011 in PCT/FR11/50905 Filed Apr. 20, 2011.

*Primary Examiner* — Mirellys Jagan
(74) *Attorney, Agent, or Firm* — Oblon, McClelland, Maier & Neustadt, L.L.P.

(57) ABSTRACT

A system for cooling and holding a testpiece in an effective manner while the testpiece is subjected locally to high heat flux. The testpiece includes an inside face extended by parallel strips that leave between them channels for passing a cooling fluid, and parallel fins of an intermediate part are inserted between the strips.

10 Claims, 3 Drawing Sheets

(56) References Cited

U.S. PATENT DOCUMENTS

2008/0192799 A1   8/2008   Deoclezian et al.
2011/0063772 A1*  3/2011   Steger ........................... 361/234
2013/0215927 A1*  8/2013   Camberlein et al. ............ 374/29
2014/0233602 A1*  8/2014   Kitazawa ........................ 374/45
2014/0286373 A1*  9/2014   Thresher et al. ................. 374/29

FOREIGN PATENT DOCUMENTS

| | | |
|---|---|---|
| EP | 1 936 354 | 6/2008 |
| FR | 2 674 333 | 9/1992 |
| GB | 2 332 747 | 6/1999 |

* cited by examiner

DEVICE EVALUATING THERMOMECHANICAL FATIGUE OF A MATERIAL

BACKGROUND OF THE INVENTION

1. Field of the Invention

The invention relates to a device for evaluating thermomechanical fatigue of a material subjected to high heat flux; the invention relates more particularly to a functional assembly enabling a sample of a given material to be subjected to such high heat flux, e.g. in order to assess the reliability of the predicted lifetime of a cryogenic rocket engine combustion chamber that is made at least in part out of the material (alloy) under consideration.

2. Description of the Related Art

An elasto-visco-plastic (EVP) type model has been developed for some years concerning the lifetime of structures that are raised to high temperature, such as for example the regenerator circuits (RC) of a cryogenic rocket engine combustion chamber, and these models are adapted to predicting the lifetimes of such structures.

It is therefore desirable to validate such an EVP lifetime model by subjecting the material of a specific testpiece to a set of loads that is as representative as possible of the real set of loads, at least concerning the imposed heat flux. The looked-for range of flux levels must be representative of that encountered in a rocket engine regenerator circuit, i.e. it must reach or indeed exceed 100 megawatts per square meter ($MW/m^2$) over a circular zone having a diameter of at least 5 millimeters (mm).

Presently known solutions make it possible to reach lower heat flux levels, of the order of about 10 $MW/m^2$. Some of them can implement complex cooling systems, e.g. making use of cryotechnical fluids, thereby requiring an installation that is complex and expensive, both in terms of design and of operation.

BRIEF SUMMARY OF THE INVENTION

The invention enables those drawbacks to be overcome.

The object of the invention is thus to put models to the test in a realistic industrial context.

Validation relies on the suitability of the developed technological testpiece for being subjected locally to high levels of heat flux so as to cause the same physical degradation phenomena to appear therein as those that are observed, by way of example, on the channels of a genuine cryogenic rocket engine regenerator circuit, namely:

deformations projecting from the hot walls of the channels; and piercing of the channels after some number of operating cycles (less than one hundred).

Only high levels of heat flux make it possible to obtain high temperatures in the thickness of the hot wall together with temperature gradients that are sufficiently steep for the viscosity of the material to have an effect.

Another object is to be able to impose such a high level of heat flux with heater means that are relatively simple, while having recourse to a cooling system that is "industrial", i.e. using a cooling fluid that is not cryotechnical, in order to guarantee trials at relatively low cost.

More particularly, the invention provides a device for evaluating thermomechanical fatigue of a material subjected to heat flux, the device being characterized in that it comprises:

a testpiece made of said material and having a "hot" wall with an outside face to be subjected to said heat flux and an inside face that is extended by parallel strips attached to said inside face and leaving parallel channels between one another;

an intermediate part having parallel fins shaped and dimensioned to become inserted in said channels between said strips in order to define a passage in the vicinity of said inside face of the hot wall for circulating cooling fluid, the passage being made up of a plurality of parallel segments separated by said strips, the section of said passage being defined by engaging said fins in said parallel channels;

a support having said testpiece and said intermediate part installed thereon and including duct elements connected to the ends of said cooling fluid circulation passage;

a cooling fluid circulation circuit connected to said duct elements; and heater means for heating said hot wall.

It should be observed that the support and said intermediate part may be combined as a single part.

Advantageously, the heater means comprise a plasma torch directed towards said outside face of said hot wall; it is preferable to use a low-pressure blown arc plasma torch.

According to another advantageous characteristic, said testpiece is made out of a block of material in which said parallel channels are formed. By way of example, these may be obtained by milling so that the hot wall is constituted essentially by the thickness of the material that is left between the bottoms of the channels and the outside face of the block.

If necessary, said testpiece includes at least one temperature sensor housed in a blind hole formed in one of the above-mentioned strips to a predetermined distance from said outside face of said hot wall. Such a sensor may be constituted by a thermocouple.

In a preferred arrangement, the parallel channels of said testpiece are longer than said fins of the intermediate part and they extend beyond the ends of the fins. As a result, the duct elements of said support lead to respective opposite ends of said intermediate part in register with said channels of the testpiece between the ends of those channels and the ends of said fins.

Preferably, the ends of the fins are rounded with curvature corresponding to the shape of the ends of the channels of said testpiece (the rounded ends of the channels being the result of them being obtained by milling) so as to define a plenum and guide chamber for said cooling fluid in register with each orifice of a duct element of said support. The cooling fluid thus flows along the above-mentioned cooling fluid flow passage in regular manner without turbulence.

By way of example, the intermediate part is interposed between the support and the testpiece. To do this, in one face said support includes a setback into which said intermediate part is inserted. More precisely, a base of the intermediate part carrying said fins is received in the setback, and the testpiece is fastened to the support so that said intermediate part is clamped between the testpiece and the support.

BRIEF DESCRIPTION OF THE SEVERAL VIEWS OF THE DRAWINGS

The invention can be better understood and other advantages thereof appear more clearly in the light of the following description given purely by way of example and made with reference to the accompanying drawings, in which.

DETAILED DESCRIPTION OF THE INVENTION

Figure 1:
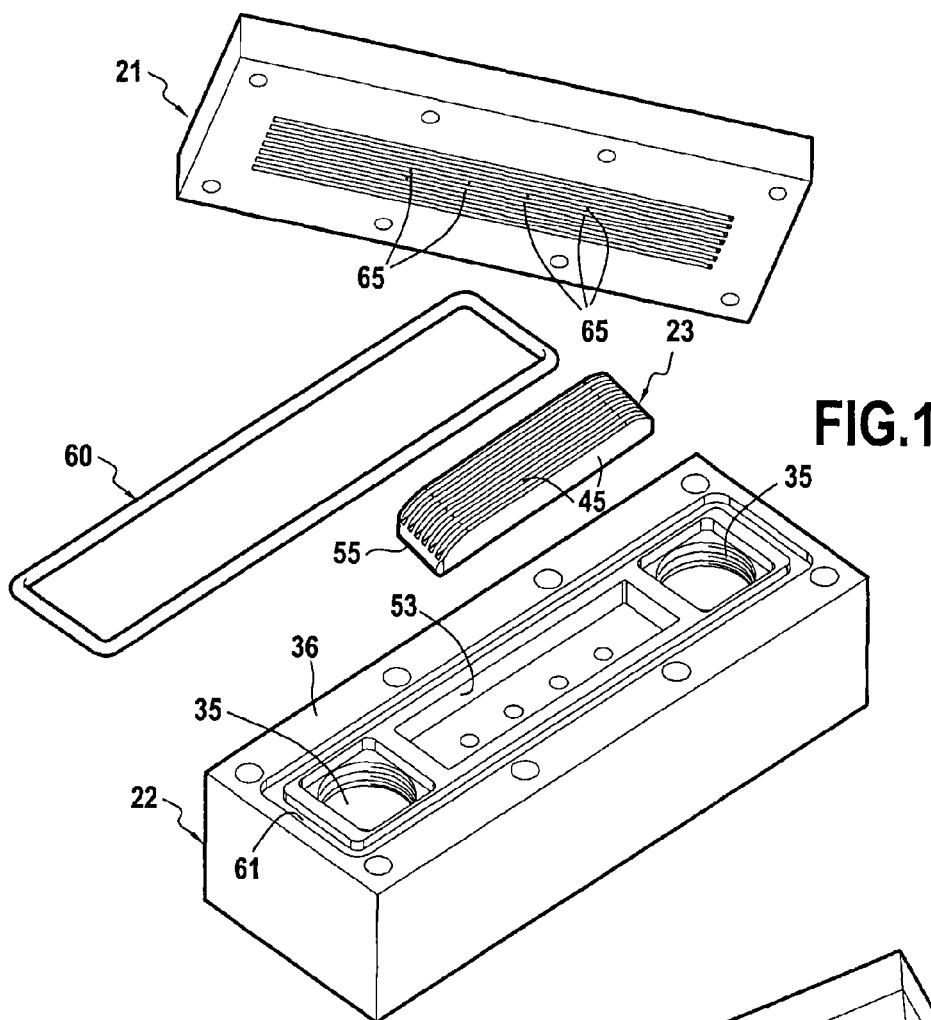
FIG. 1 is a general diagrammatic view in exploded perspective showing a portion of the device.

As shown, the device in accordance with the invention comprises an enclosure 11 in which vacuum can be made and that contains a plasma torch 13 carried by a controlled robot arm 15 and, facing it, a test subassembly 20 constituted by a testpiece 21 assembled with a support 22 and an intermediate part 23 having a comb-shaped profile, as described below. The subassembly is installed at the end of a post 25 so that an outside face of a wall of the testpiece 21, referred to as the "hot" wall 27, is exposed to the heat flux delivered by the plasma torch 13. The support part 22 is advantageously fastened to the post 25 by using two screws 37 for this purpose, which screws are situated on an edge between the two cooling fluid feed orifices 35. These two screws thus serve not only to hold the testpiece 21 on the support 22, but also to fasten the support 22 on the post 25 without it being necessary to provide another interface on the part 22. The testpiece 21 can be made to occupy only one position on the support 22 by using a centering peg (not shown) between these two elements. This is advantageous from an experimental point of view.

The robot is programmed so that said torch can move over said hot wall, extending perpendicularly thereto. A plurality of regions of the rectangular hot wall of the testpiece can thus be subjected to the action of the plasma torch.

The testpiece 21 is made of the material that is to be tested. The hot wall 27 is relatively thin and its bottom face 31 is extended by parallel strips 29. These are attached to said bottom face and they leave parallel channels 33 between one another. In the example shown, the testpiece is made in a block of said material that is in the form of a rectilinear parallelepiped (e.g. in a block of a copper-based alloy), with the parallel channels 33 being formed therein, advantageously by milling. As a result, the ends of the parallel channels are rounded, as shown.

Figure 2:
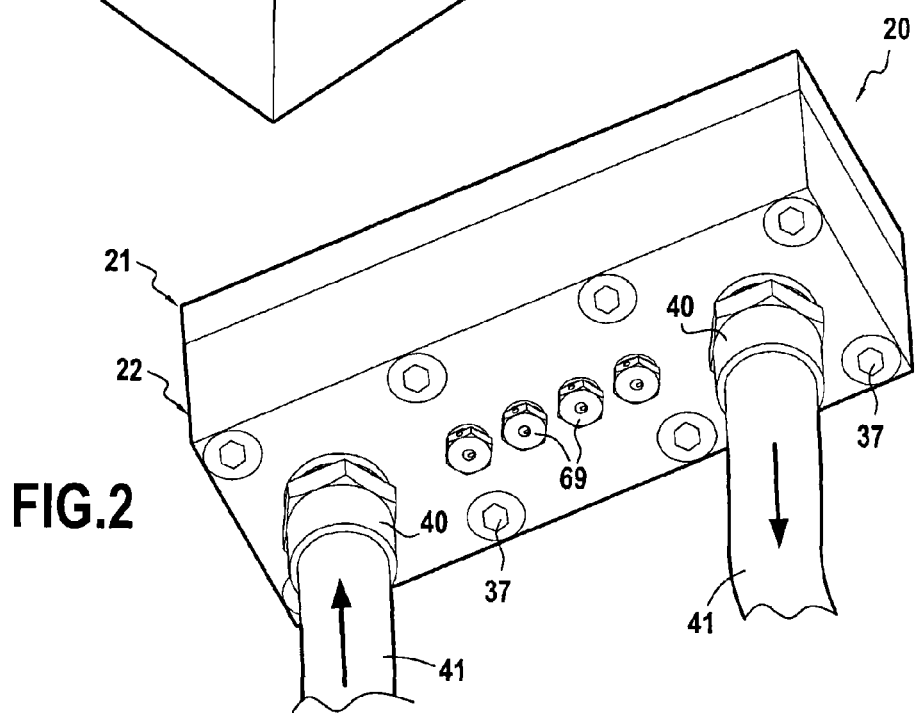
FIG. 2 shows the same portion, in perspective, as seen from below.

The support 22 that receives said testpiece 21 is in the form of a block that is machined to have the shape of a rectangular parallelepiped, and at its ends it includes duct elements 35 opening out into the face 36 on which the testpiece 21 is fastened by a set of screws 37. The duct elements 35 are internally tapped and they serve to mount couplings 40 that project from the face of the support opposite from the face on which the testpiece is mounted. As shown in FIG. 2, these two couplings are connected to pipes 41 that pass in leaktight manner through the wall of the enclosure 11 that is evacuated. The ducts are connected to an external unit 43 comprising a tank of cooling fluid and a pressure-raising unit, e.g. constituted by at least one pump.

Advantageously, the cooling circuit may be a closed circuit that may also include a fluid refrigeration system seeking to maintain the temperature of said fluid at the inlet 35 of the testpiece at a temperature that is regulated within a determined range. On this principle, the cooling fluid may for example be refrigerated distilled water that is caused to circulate at a service pressure of several tens of bars.

Figure 6:
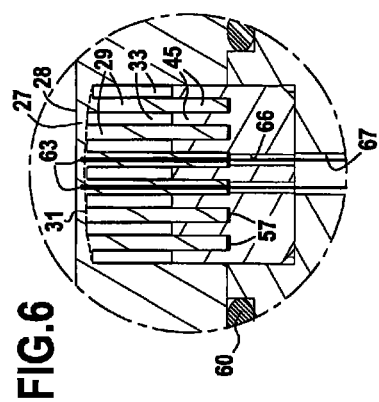
FIG. 6 is a larger scale view of a box VI in FIG. 5.
Figure 5:
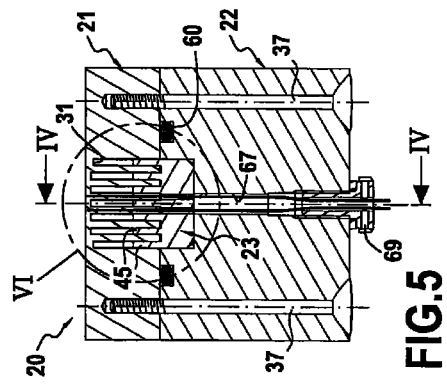
FIG. 5 is a section on V-V of FIG. 4.
Figure 3:
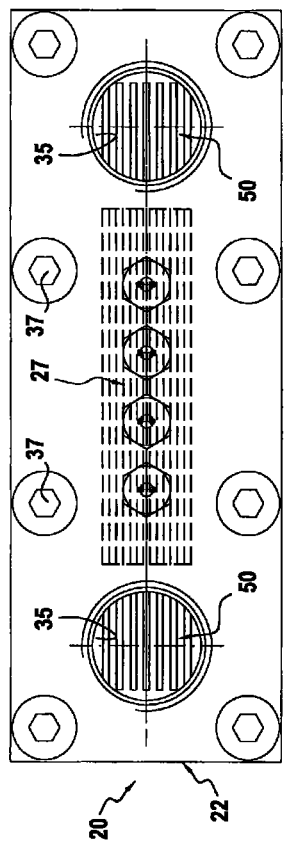
FIG. 3 is a plan view from below of the same portion.
Figure 4:
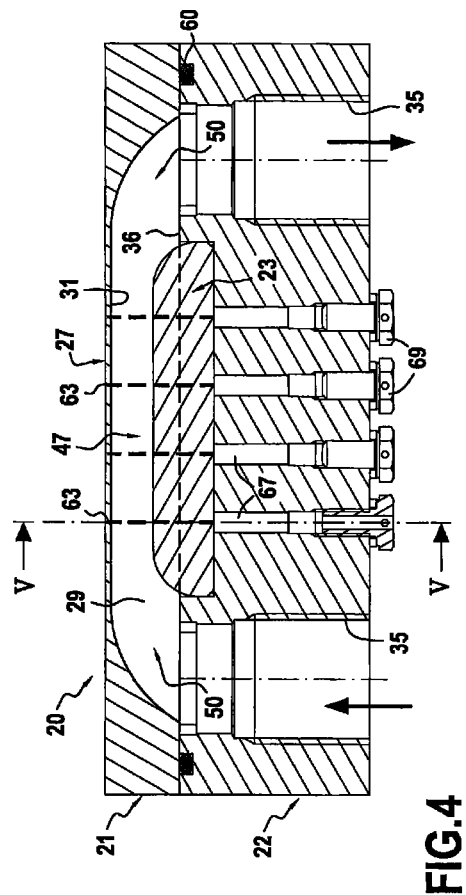
FIG. 4 is a section on IV-IV of FIG. 5.
Figure 7:
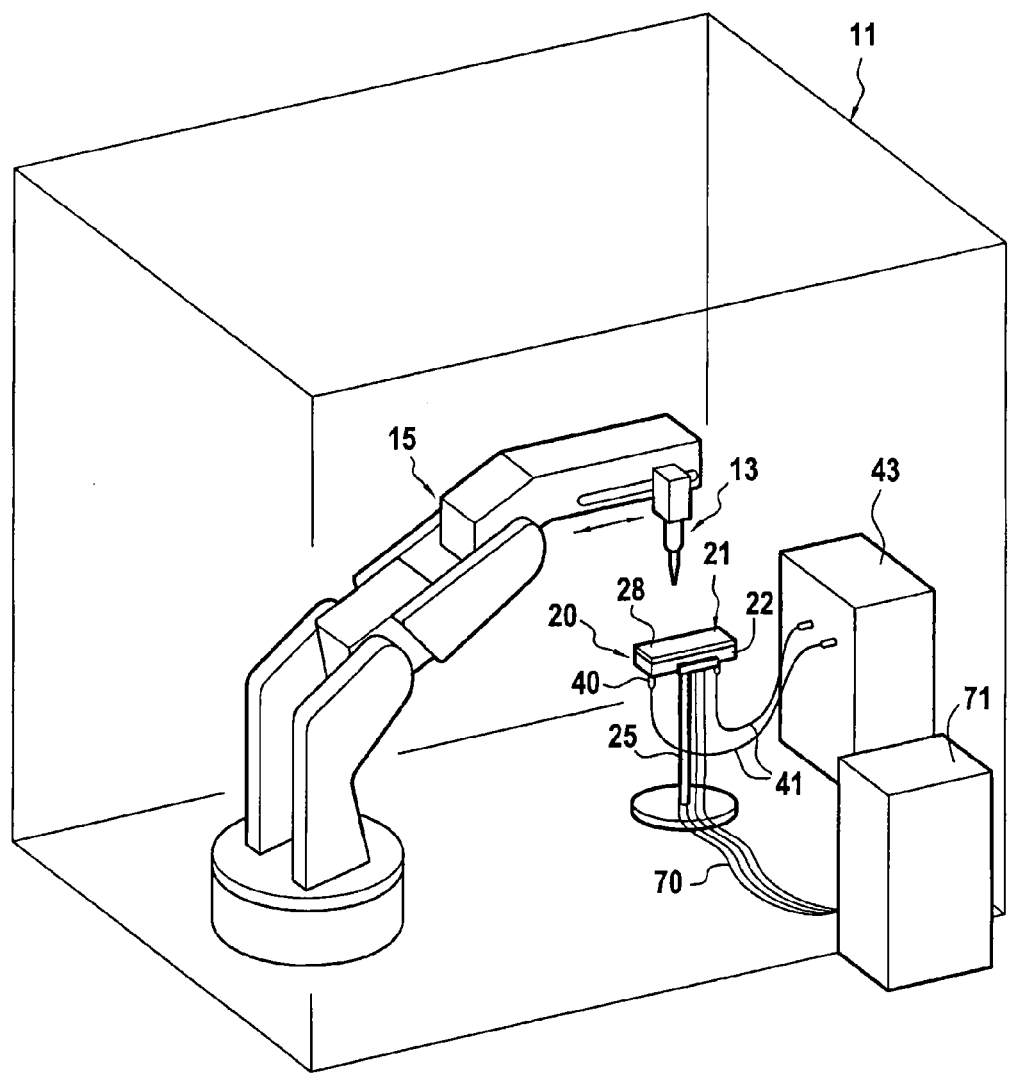
FIG. 7 is a diagrammatic view of the device as a whole shown while in operation.

The intermediate part 23 having a comb-shaped profile (in a right cross-section perpendicular to its longitudinal direction, see FIG. 6) comprises parallel fins 45 shaped and dimensioned to become inserted in said channels 33 between the strips 29. The thickness of the fins corresponds substantially to the width of the channels in the testpiece 21. The height of the fins is determined so as to determine a cooling fluid passage 47 of predetermined section in the vicinity of said inside face 31 of the hot wall, which section is thus made up of a plurality of parallel segments separated by said strips 29. The flow section of said passage all along said hot wall is defined by engaging said fins 45 in said parallel channels 33, it being understood that the fins present an engagement height that is less than the depth of the channels. In the example shown, the fins of the intermediate part are machined as a function of the section desired for the cooling fluid flow passage so that the strips of the testpiece come as close as possible to face the bottoms of the groove in said intermediate part formed between said fins, doing so with clearance that is small but not zero.

From the above description, it can be seen that the width of said hot wall is limited in the bulk of the testpiece by the parallel channels 33 that are milled therein. The milling depth of the channels determines the thickness of the hot wall between the bottoms of the parallel channels and the outside face 28 of the testpiece. For reasons of mechanical strength while being stressed by pressure and the thermal load, the longitudinal edges of the hot wall are of greater thickness; the extra thickness is about 50%. This may be obtained by ensuring that the two outside parallel channels 33 of the testpiece are not as deep as the middle channels, of which there are five in this example, thereby enabling the thickness of the hot wall 27 to be effectively increased along its longitudinal edges, as can be seen in FIG. 6. The natural overall deformation of the hot wall during testing consists generally in bulging under the combined effect of the differential thermal expansion between the heated outside surface and the cooled inside surface. This bulging is also encouraged by the effect of the internal pressure of the cooling fluid. The extra thickness of the hot wall 27 along its longitudinal edges serves to avoid rupture.

In one method of using the invention, the strips of the testpiece may advantageously be stuck by epoxy resin to the bottoms of the grooves in the intermediate part.

Such adhesive bonding serves to limit or even to eliminate the above-described phenomenon of the heated wall 27 bulging. However such adhesive assembly does not prevent the design being suitable for dismantling, since the adhesive can be eliminated by stoving at an appropriate temperature.

Furthermore, the parallel channels 33 of the testpiece are longer than the fins 45 of the intermediate part 23 and they extend beyond the ends of said fins. Consequently, the duct elements 35 of the support at opposite ends of said intermediate part 23 lead into respective ends of the channels 33 in the testpiece. Each duct element 35 opens out between the ends of said channels 33 and the ends of said fins 45. Furthermore, and as shown, the ends of the fins are rounded so as to correspond to the shape of the ends of the channels in the testpiece (with these rounded ends being the result of said channels being milled). As a result, facing each orifice of a duct element 35 in said support 22 there is a respective plenum and guide chamber 50 for the cooling fluid so as to enable said fluid to flow in non-turbulent manner through the above-mentioned cooling fluid flow passage 47 defined in the vicinity of the bottom face 31 of the hot wall.

The intermediate part 23 is clamped between the support 22 and the testpiece 21 when the testpiece is fastened to said support by the screws 37. More particularly, the support includes an insertion setback 53 for receiving the intermediate part 23 in a face for mounting the testpiece. A base 55 of the intermediate part carries the fins 45 and is engaged in the setback. Said intermediate part is thus prevented from moving between the bottom of said setback and the edge faces of said strips 29 of the testpiece. As mentioned above, assembly may be improved by placing epoxy resin 57 on the edge faces of the strips, during assembly, so as to limit the extent to which bulging of the heated wall 27 occurs.

Furthermore, the support 22 and the testpiece 21 are fastened together with an interposed sealing gasket 60 surrounding both the orifices of said duct elements 35 and said setback 53 receiving the base 55 of the intermediate part. This gasket is received in a groove of closed outline 61 formed in the face of the support that receives the testpiece.

It may be advantageous to know the temperature of the hot wall 27 during operations. For this purpose, said testpiece includes at least one temperature sensor 63, e.g. of the thermocouple type.

In the example shown, four pairs of longitudinally spaced-apart temperature sensors 63 are provided. Each pair of temperature sensors serves to define a test zone on a given testpiece in which it is possible to observe how temperature varies during a test. Four test zones are thus provided that are longitudinally spaced apart, with each of these zones presenting the same cooling conditions and thus the same capacities for being stressed. Each zone is thus fitted with two thermocouples 63 to provide measurement redundancy. More particularly, and as shown, such a sensor (thermocouple) is housed in a blind hole 65 formed in a strip 29 of the testpiece to within a predetermined distance from said outside face 28 of the hot wall. Through holes formed in the intermediate part 23 and in the support 22 serve to pass electric wires that are connected to the sensor. More precisely, for each sensor, the intermediate part 23 has a through hole 66 formed through its base 55 and opening out between two of its fins 45, in register with a corresponding blind hole 65. The support has a through hole 67 for each pair of sensors, the through hole 67 having a greater diameter and serving to provide communication with both of the adjacent holes 66 in the intermediate part. At the back of the support, threaded plugs 69 are engaged in tapping in these holes. They include drilled holes for passing electric wires 70. The positions of the sensors are preferably made permanent by injecting epoxy resin into the holes containing them.

The electric wires are connected to a measurement unit 71.

For the various zones defined in the hot wall 27 around the locations of the pairs of sensors, it may be advantageous to place the sensors at different depths beneath the outside face of the hot wall, e.g. at depths of 0.5 mm, 1 mm, 2 mm, and 3 mm beneath said outside face 28 of the hot wall 27, so as to obtain information about temperatures at different depths in the hot wall. For this purpose, it suffices to adjust accordingly the depths of the blind holes 65 for any pair of sensors. Duplicating the measurement channels serves advantageously to make the temperature measurements more reliable.

The way a test is performed can be seen clearly from the above description. A subassembly 20 such as that defined above is installed on the end of the post 25 that is situated inside the enclosure 11. The cooling fluid circulation circuit is connected, and a vacuum is established in the enclosure prior to putting the plasma torch 13 into operation. The plasma torch is directed perpendicularly to the surface of the hot wall.

Distilled water is caused to flow in the circuit so as to cool the inside face of the hot wall continuously while its outside face is being subjected to the heat flux generated by the plasma torch. The plasma torch is moved over the hot wall by causing the robot arm 15 to move. The rate of approach of the torch, its minimum distance from the hot wall, and the length of time the wall is exposed to the heat flux constitute parameters for adjusting the trial so as to make it possible to implant multiple forms of thermal stressing that are representative of different aspects of the operation of a rocket engine (thermal transients that are fast, slow, stabilized, change in the level of the heat flux, etc. . . . ).

Because of its comb-shaped profile, the intermediate part 23 serves to hold the parallel strips of the testpiece by preventing them from twisting or pivoting when the hot wall deforms. Thus, the spacing between the strips 29 is guaranteed, thereby avoiding any effect of closing or varying the section of said cooling fluid flow passage defined between the strips 29 and the fins of the intermediate part.

Naturally, other variants are possible, concerning both the heater means and the cooling means.

It should be observed that the above-described device is of low cost and can be used during a series of tests. Only the testpiece needs to be changed from one trial to another, and each testpiece enables several different tests to be performed.

The invention claimed is:

1. A device for evaluating thermomechanical fatigue of a material subjected to heat flux, comprising:
   a testpiece made of the material and including a hot wall with an outside face to be subjected to the heat flux and an inside face that is extended by parallel strips attached to the inside face and leaving parallel channels between one another;
   an intermediate part including parallel fins shaped and dimensioned to become inserted in the channels between the strips to define a passage in a vicinity of the inside face of the hot wall for circulating cooling fluid, the passage including a plurality of parallel segments separated by the strips, a section of the passage being defined by engaging the fins in the parallel channels;
   a support including the testpiece and the intermediate part installed thereon and including duct elements connected to ends of the cooling fluid circulation passage;
   a cooling fluid circulation circuit connected to the duct elements; and
   heater means for heating the hot wall.

2. A device according to claim 1, wherein the testpiece includes at least one temperature sensor.

3. A device according to claim 1, wherein outer parallel channels of the testpiece are shallower than middle channels, thereby increasing a thickness of the hot wall along its longitudinal edges.

4. A device according to claim 1, wherein the support includes, on one face, a setback for receiving the intermediate part, in which a base of the intermediate part is received, the base carrying the fins, wherein the testpiece is fastened to the support so as to clamp the intermediate part between the testpiece and the support, and wherein the support and the testpiece are fastened to each other with a sealing gasket interposed between them that surrounds the orifices of the duct elements and the setback receiving the base.

5. A device according to claim 1, wherein the heater means comprises a plasma torch directed towards the outside face of the hot wall.

6. A device according to claim 5, wherein the plasma torch and the subassembly constituted by assembling together the testpiece, the intermediate part, and the support are installed in a vacuum enclosure, and wherein the plasma torch is carried by a robot arm that is controlled to adjust a position and movement of the plasma torch relative to the hot wall.

7. A device according to claim 1, wherein the testpiece is made out of a block of material in which the parallel channels are formed.

8. A device according to claim 7, wherein the testpiece includes at least one temperature sensor, and wherein the at least one temperature sensor is housed in a blind hole formed in a strip extending to a predetermined distance from the outside face of the hot wall together with through holes formed in the intermediate part and in the support for passing electric wires connected to the sensor.

9. A device according to claim 1, wherein the parallel channels of the testpiece are longer than the fins of the intermediate part and extend beyond ends of the fins, the duct elements of the support leading to respective ends of the intermediate part in register with the channels of the testpiece, between ends of the channels and ends of the fins.

10. A device according to claim 9, wherein the ends of the fins are rounded so as to correspond to a shape of the ends of the channels of the testpiece as results from the channels being milled and so as to define a plenum and guide chamber for the cooling fluid in register with each orifice of a duct element of the support.

\* \* \* \* \*